United States Patent [19]
Griffin

[11] Patent Number: 5,108,686
[45] Date of Patent: Apr. 28, 1992

[54] METHOD OF REPLICATING A HUMAN NIPPLE FOR USE AS A NURSING DEVICE

[76] Inventor: Joyce B. Griffin, 6050 Westside Rd., Healdsburg, Calif. 95448

[21] Appl. No.: 670,047

[22] Filed: Mar. 15, 1991

[51] Int. Cl.$^5$ .............................................. B29C 33/38
[52] U.S. Cl. .................................. 264/222; 215/11.1; 264/138; 264/227; 264/255; 606/236
[58] Field of Search ............... 264/219, 222, 227, 255, 264/DIG. 30, 138, 220, 225, 226; 215/11.1; 606/236, 234, 235; 425/2

[56] References Cited

U.S. PATENT DOCUMENTS

| | | | |
|---|---|---|---|
| 2,129,304 | 9/1938 | Feinbloom | 264/222 |
| 2,580,264 | 12/1951 | Wright et al. | 264/222 |
| 3,811,133 | 5/1974 | Harris | 264/222 |
| 4,019,209 | 4/1977 | Spence | 264/DIG. 30 |
| 4,086,666 | 5/1978 | Vaskys et al. | 264/222 |
| 4,317,241 | 3/1982 | Knoche | 264/222 |
| 4,401,492 | 8/1983 | Pfrommer | 264/222 |
| 4,600,551 | 7/1986 | Erb | 264/222 |
| 4,676,386 | 6/1987 | Phlaphongphanich | 215/11.1 |
| 4,830,205 | 5/1989 | Hammond et al. | 215/11.1 |

FOREIGN PATENT DOCUMENTS 3232506  3/1984  Fed. Rep. of Germany ...... 606/236

Primary Examiner—Jay H. Woo
Assistant Examiner—Robert B. Davis
Attorney, Agent, or Firm—Larry D. Johnson

[57] ABSTRACT

A nursing device provides a nursing or pacifier nipple for use with nursing infants, and a method for manufacturing such articles. The device comprises an exact replica of the mother's nipple incorporated onto a bottle, specialized dispenser, or pacifier. The nursing device is formed from a mold taken of the nursing mother's natural breast and nipple.

6 Claims, 2 Drawing Sheets

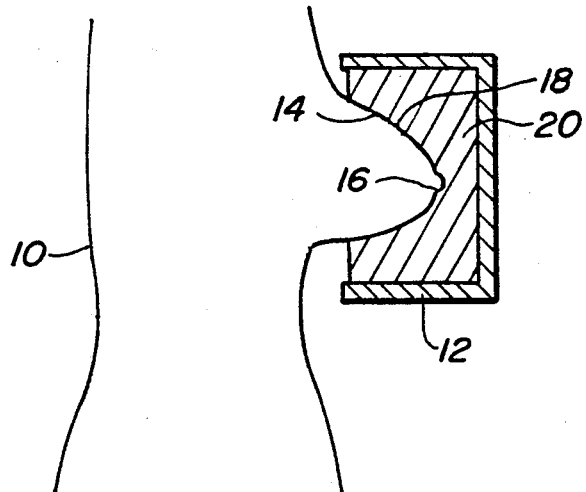
FIG._1
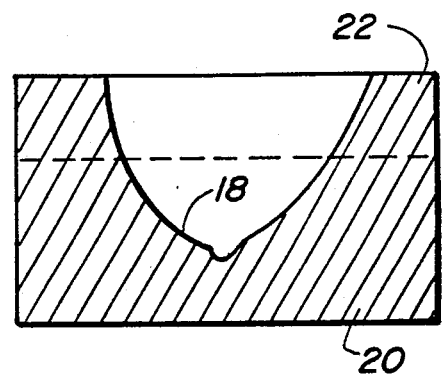
FIG._2
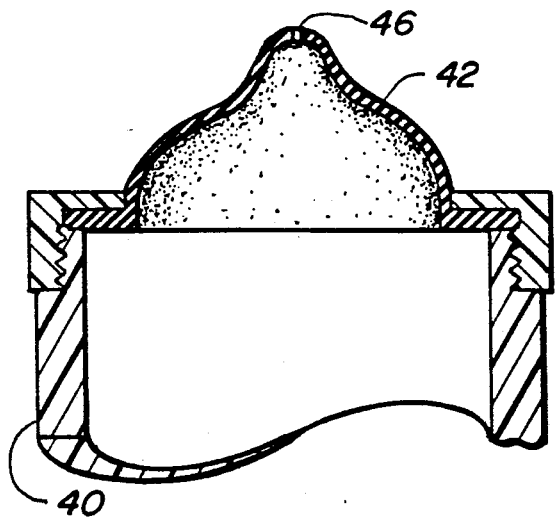
FIG._6
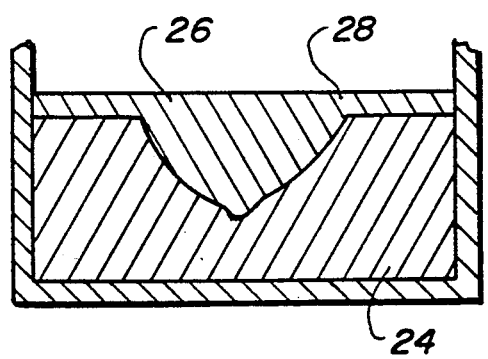
FIG._3
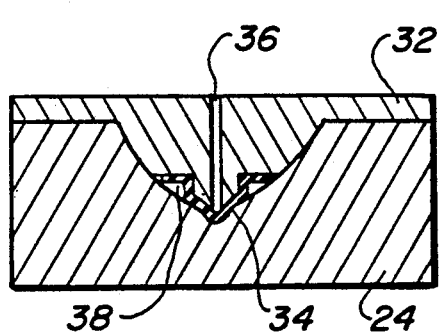
FIG._5
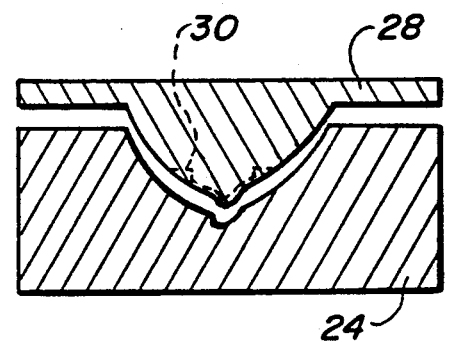
FIG._4

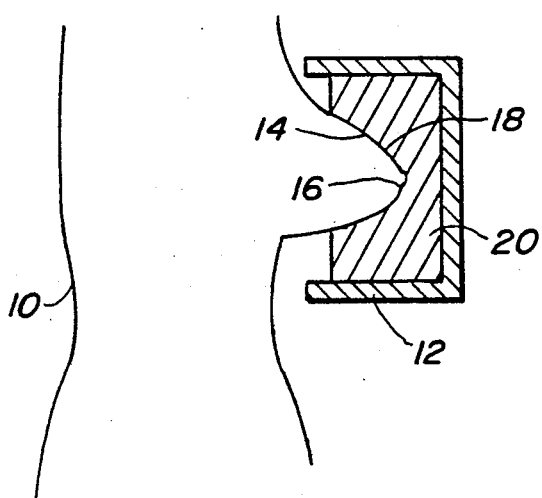
FIG._7
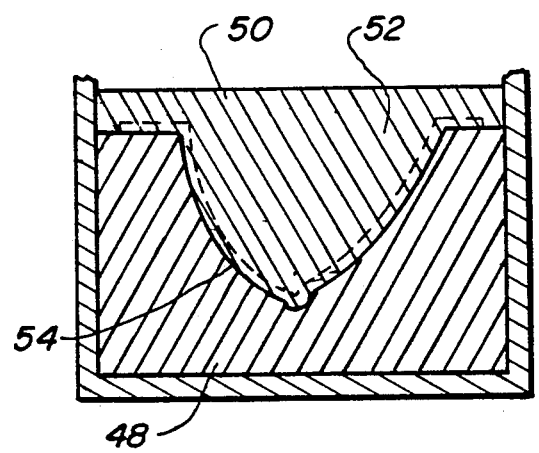
FIG._8
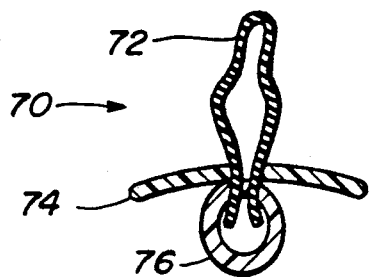
FIG._12
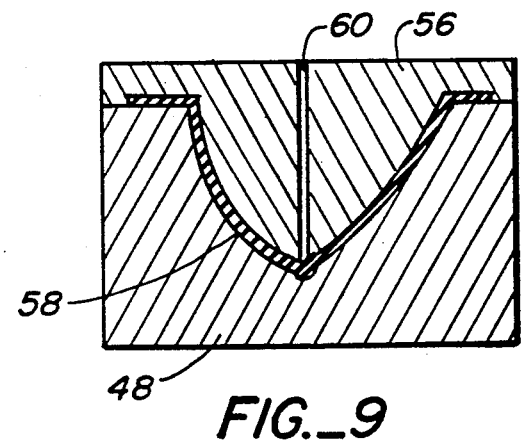
FIG._9
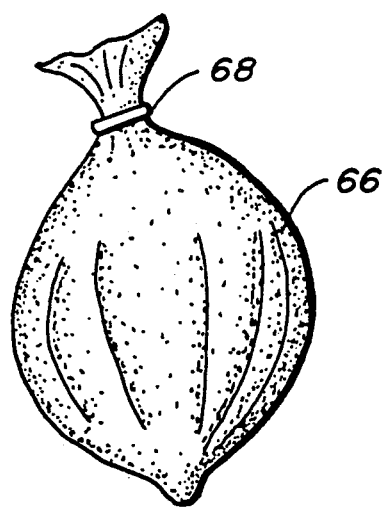
FIG._11
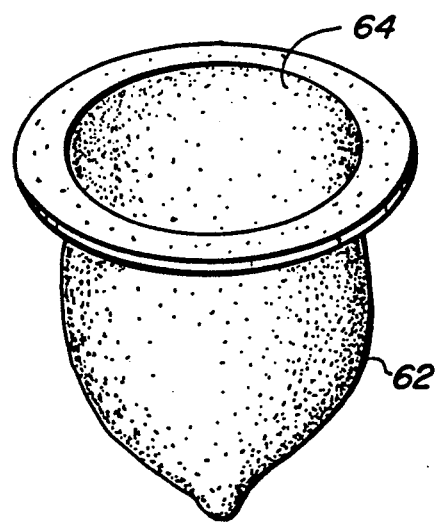
FIG._10

METHOD OF REPLICATING A HUMAN NIPPLE FOR USE AS A NURSING DEVICE

BACKGROUND OF THE INVENTION

1. Field of the Invention

This invention relates generally to infant feeding articles and accessories, and more specifically to an improved method and apparatus for nursing infants.

2. Description of the Prior Art

Not all mothers are able to nurse their infants. Non-nursing mothers who for whatever reason are unable to breast feed their infants often feel guilty or intimidated about the quality of their parenting. The concept of bottle-feeding their infants seems distant and impersonal.

Of course, even nursing mothers sometimes need to leave their infants for a period of time, and may therefore miss a regularly scheduled feeding. In such situations, the nursing mother may choose to milk her breasts and leave the bottled food with a sitter. However, small babies often do not readily accept a bottle after having been nursed at the breast, regardless of the fact that the milk in the bottle is their own mother's milk. Therefore, it is likely that the shape and texture of the bottle nipple causes or at least contributes to the rejection.

SUMMARY OF THE INVENTION

The nursing device of this invention provides an improved nursing and/or pacifier nipple for use with nursing infants, as well as a method for manufacturing such articles. The nursing device comprises an exact replica of the mother's nipple incorporated onto a baby's bottle or pacifier, and which is formed from a mold taken of the nursing mother's natural breast and nipple. Sets of individualized nipples may be prepared for a nursing mother by a medical practitioner, or by the consumer herself.

During various stages of growth and development, when the mother, attending physician or nurse, notes significant changes in the nursing mother's nipple, a new mold can be made and replacement nipples reproduced as required. For example, a first mold might be taken immediately after the birth of the infant to create a nipple to be used for the first few days, after which a second mold may be taken to make nipples for use through approximately six months of age, followed by a third mold taken to make nipples for use thereafter.

All mothers of newborn infants and small babies are candidates for this method. Today's parents want to provide the least stress for their babies in every possible situation, particularly the simple and obvious. The parents know that the less trauma for the infant, the better the childrearing. One simple way to reduce infant frustration is providing mother's nipple on baby's bottle.

While most babies will eventually accept a standard manufactured bottle nipple after repeated forcing, it is this very discomfort and anxiety that the nursing device of this invention avoids through the use of a personalized nipple. The baby will not suffer the same agony of not having mother's breast at hand. In addition, the nursing mother is relieved of the guilt of leaving her child with a surrogate, as well as when making the larger transition from breast to bottle.

The mother who is unable to nurse at all can feel closer attachment and intimacy by having her own nipple duplicated for her baby's feeding. Thus, the personalized nipple is a positive and healthy addition to better parenting, but does not advocate bottle feeding over breast feeding.

BRIEF DESCRIPTION OF THE DRAWINGS

FIGS. 1-6 are a series of views illustrating a method of manufacturing a bottle nipple embodiment of the nursing device of this invention;

FIG. 1 is a diagrammatic view of a profile in section of a woman's body, showing a mold in cross-section placed over the natural breast and nipple to create an impression in the casting material;

FIG. 2 is a side elevation cross-sectional view of the casting material bearing the impression of the natural breast and nipple, illustrating the excess material of the cast to be removed to produce a final working negative cast of the natural breast and nipple;

FIG. 3 is a side elevation cross-sectional view of the final working negative cast as replaced within the mold, and filled with a further casting material to produce a positive cast of the breast and nipple;

FIG. 4 is a side elevation cross-sectional view of the final working negative cast and the positive cast of the breast and nipple, and illustrating in phantom the casting material to be removed from the positive cast to produce a final working positive cast of the breast and nipple;

FIG. 5 is a side elevation cross-sectional view of the final working negative and positive casts as mated to define a cavity within, and being used as a mold to produce a cast article in the cavity, this view further illustrating a sprue in the positive cast for entry of the material used to form a finished nursing device, and a step-forming ring inserted into the cavity to create a desired step in the finished nursing device; and FIG. 6 is a cross-sectional view of the upper portion of an infant's bottle bearing the bottle nipple embodiment of the finished nursing device of this invention;

FIGS. 7-11 are a series of views illustrating a method of manufacturing a self-contained embodiment of the nursing device of this invention;

FIG. 7 is a diagrammatic view of a profile in section of a woman's body, showing a mold in cross-section placed over the natural breast and nipple to create an impression in the casting material, this view analogous to FIG. 1;

FIG. 8 is a side elevation cross-sectional view of a final working negative cast, filled with a further casting material to produce a positive cast of the breast and nipple, and illustrating in phantom the casting material to be removed from the positive cast to produce a final working positive cast of the breast and nipple;

FIG. 9 is a side elevation cross-sectional view of the final working negative and positive casts as mated to define a cavity within, and being used as a mold to produce a cast article in the cavity, this view further illustrating a sprue in the positive cast for entry of the material used to form a finished nursing device;

FIG. 10 is a perspective view of a relatively rigid "pluggable" version of a finished self-contained embodiment of the nursing device of this invention; and FIG. 11 is a perspective view of a relatively non-rigid "closeable" version of a finished self-contained embodiment of the nursing device of this invention; and FIG. 12 is a side elevation cross-sectional view of a pacifier embodiment of the nursing device of this invention.

DETAILED DESCRIPTION OF A PREFERRED EMBODIMENT

FIGS. 1-6 are a series of views illustrating a method of manufacturing a bottle nipple embodiment of the nursing device of this invention. FIG. 1 is a diagrammatic view of a profile in section of a woman's body 10, showing a mold 12 in cross-section placed over the natural breast 14 and nipple 16 to create an impression 18 in the casting material 20. The particular mold and casting material used may be of any appropriate type, suitable for rendering a realistic impression of the natural breast and nipple.

FIG. 2 is a side elevation cross-sectional view of the casting material 20 bearing the impression 18 of the natural breast and nipple, illustrating some portion 22 of excess material of the cast to be removed to produce a final working negative cast of the natural breast and nipple. The amount of excess material to be removed is determined both by the depth of the original cast, and the desired size of the ultimate end-product.

FIG. 3 is a side elevation cross-sectional view of the final working negative cast 24 as replaced within the mold 12, and filled with a further casting material 26 to produce a positive cast 28 of the breast and nipple. Appropriate casting material and technology is employed to ensure release of the two casts.

FIG. 4 is a side elevation cross-sectional view of the final working negative cast 24 and the positive cast 28 of the breast and nipple, and illustrating in phantom the casting material 30 to be removed from the positive cast to produce a final working positive cast of the breast and nipple. The quantity of material to be removed is determined by the size and shape of the desired end-product.

FIG. 5 is a side elevation cross-sectional view of the final working negative and positive casts 24, 32, respectively, as mated to define a cavity 34 within, and being used as a mold to produce a cast article in the cavity, this view further illustrating a sprue 36 in the positive cast 32 for entry of the material used to form the finished nursing device, and a step-forming ring 38 inserted into the cavity 34 to create a desired step in the finished nursing device.

The material used to form the finished article may be any liquid or plastic substance suitable for use in a baby's nipple, such as natural latex rubber or its equivalent. Ideally, the material used should simulate the mother's natural nipple in texture, surface quality, resiliency, and rigidity. In fact, different types of latex (or other material) having different characteristics may be used in the same article. For example, a more resilient material may be used to form the nipple itself, with a less resilient material used to form the remainder of the article, which may more faithfully reflect the characteristics of the mother's natural breast and nipple.

FIG. 6 is a cross-sectional view of the upper portion of an infant's bottle 40 bearing the bottle nipple 42 as created by the aforementioned steps. Bottle nipple 42 is thus an accurate reproduction of the nursing mother's natural breast and nipple. The nipple should of course include some perforations 46 to enable passage of liquid from the bottle.

FIGS. 7-11 are a series of views illustrating a method of manufacturing a self-contained embodiment of the nursing device of this invention. FIG. 7 is a diagrammatic view of a profile in section of a woman's body 10, showing a mold 12 in cross-section placed over the natural breast 14 and nipple 16 to create an impression 18 in the casting material 20, this view being analogous to FIG. 1.

FIG. 8 is a side elevation cross-sectional view of a final working negative cast 48, filled with a further casting material 50 to produce a positive cast 52 of the breast and nipple, and illustrating in phantom the casting material 54 to be removed from the positive cast 52 to produce a final working positive cast of the breast and nipple. As before, the amount of casting material to be removed is determined by the size (e.g., thickness) and shape of the finished article to be cast.

FIG. 9 is a side elevation cross-sectional view of the final working negative and positive casts 48, 56, respectively, as mated to define a cavity 58 within, and being used as a mold to produce a cast article in the cavity, this view further illustrating a sprue 60 in the positive cast 56 for entry of the material used to form a finished nursing device.

FIG. 10 is a perspective view of a relatively rigid "pluggable" version 62 of a finished self-contained embodiment of the nursing device of this invention. This version may be made of a material and/or thickness to retain its general shape, and could be plugged or otherwise sealed at opening 64 to act as its own dispenser/container.

FIG. 11 is a perspective view of a relatively non-rigid "closeable" version 66 of a finished self-contained embodiment of the nursing device of this invention. This version may be made of a material and/or thickness to collapse or conform to any particular shape (e.g., as an insert to a rigid-walled baby bottle), and could be sealed by band or clip member 68 to act as its own dispenser/container.

FIG. 12 is a side elevation cross-sectional view of a pacifier embodiment 70 of the nursing device of this invention. The pacifier includes a nipple portion 72 made in the same manner described previously, or cut from a larger end-product such as the self-contained embodiments of FIG. 10 or FIG. 11. The pacifier further includes a shield 74 and ring or other retaining means 76, as with other standard pacifiers.

While this invention has been described in connection with preferred embodiments thereof, it is obvious that modifications and changes therein may be made by those skilled in the art to which it pertains without departing from the spirit and scope of the invention. For example, a cast article could also be made exclusively from an impression in a negative cast by simply spraying or otherwise applying an adequate thickness of latex over the negative impression, without the use of a complementary positive cast. Alternatively, the original impression (i.e., negative cast) could be created by other methods, such as by optical scanning of the breast and nipple area, which generated data could then be used to mechanically form the negative cast by well-known means. Accordingly, the scope of this invention is to be limited only by the appended claims.

What is claimed as invention is:

1. A method of manufacturing a nursing device for a nursing infant, said method comprising the steps of:
    making an impression of a mother's breast and nipple in a casting material;
    creating a cast article in said casting material that generally replicates said mother's breast and nipple by placement of a second casting material into said impression to form a positive cast, removal of some portion of said positive cast to define a cavity between said positive cast and said impression, placement of a plastic material into said cavity to form a cast article, and removal of said cast article from said cavity; and attaching said cast article to a baby bottle to serve as a nipple.

2. The method of manufacturing a nursing device of claim 1 wherein said plastic material comprises natural latex rubber.

3. The method of manufacturing a nursing device of claim 1 wherein said nursing device includes perforations to enable passage of a liquid from said baby bottle through said nursing device.

4. The method of manufacturing a nursing device of claim 1 wherein said nursing device is sealable to form a self-contained nursing device.

5. A method of manufacturing a nursing device for a nursing infant, said method comprising the steps of:
   making an impression of a mother's breast and nipple in a casting material;
   creating a cast article in said casting material that generally replicates said mother's breast and nipple by placement of a second casting material into said impression to form a positive case, removal of some portion of said positive cast to define a cavity between said positive cast and said impression, placement of a plastic material into said cavity to form a cast article, and removal of said cast article from said cavity; and
   attaching a shield portion to said cast article for use as a pacifier.

6. The method of manufacturing a nursing device of claim 5 wherein said plastic material comprises a natural latex rubber.

* * * * *